United States Patent
Chappel et al.

(10) Patent No.: US 9,901,678 B2
(45) Date of Patent: Feb. 27, 2018

(54) PUMPING DEVICE HAVING IMPROVED EMPTYING DETECTION FEATURES

(71) Applicant: DEBIOTECH S.A., Lausanne (CH)

(72) Inventors: Eric Chappel, Versonnex (FR); Frédéric Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 551 days.

(21) Appl. No.: 14/375,075

(22) PCT Filed: Feb. 1, 2013

(86) PCT No.: PCT/IB2013/050868
§ 371 (c)(1),
(2) Date: Jul. 28, 2014

(87) PCT Pub. No.: WO2013/114331
PCT Pub. Date: Aug. 8, 2013

(65) Prior Publication Data
US 2015/0011940 A1    Jan. 8, 2015

(30) Foreign Application Priority Data

Feb. 1, 2012   (EP) ..................................... 12153541

(51) Int. Cl.
*A61M 1/00*  (2006.01)
*A61M 5/168* (2006.01)
*A61M 5/145* (2006.01)
*A61M 5/142* (2006.01)

(52) U.S. Cl.
CPC .......... *A61M 5/1684* (2013.01); *A61M 5/145* (2013.01); *A61M 5/14248* (2013.01);
(Continued)

(58) Field of Classification Search
CPC ...... A61M 2205/0266; A61M 2205/18; A61M 2205/3331; A61M 2205/3386;
(Continued)

(56) References Cited

U.S. PATENT DOCUMENTS 8,070,745 B2* 12/2011 Gibson ............. A61M 5/14276
                                                         604/133
8,603,051 B2* 12/2013 Kuo ..................... A61M 5/1407
                                                         604/288.01
(Continued)

FOREIGN PATENT DOCUMENTS

CN         1471413 A      1/2004
EP         1 839 695      10/2007
(Continued)

OTHER PUBLICATIONS

International Search Report for PCT/IB2013/050868 dated Aug. 5, 2013.
Written Opinion of the International Searching Authority for PCT/IB2013/050868 dated Aug. 5, 2013.

*Primary Examiner* — Rebecca E Eisenberg
(74) *Attorney, Agent, or Firm* — Nixon & Vanderhye P.C.

(57) ABSTRACT

Sensor for dynamically detecting the residual fluid volume $V_{res}$ of a collapsible reservoir (1,3) characterized by the fact that it is adapted to detect a threshold pressure $P_{th}$ which corresponds to a phase within said reservoir (1,3) when only said residual fluid volume $V_{res}$ remains, said residual volume $V_{res}$ corresponding to a safety volume sufficient to ensure a safety margin to alert the user before the reservoir (1,3) is empty.

27 Claims, 13 Drawing Sheets

(52) U.S. Cl.
CPC . *A61M 2205/0266* (2013.01); *A61M 2205/18* (2013.01); *A61M 2205/3331* (2013.01); *A61M 2205/3386* (2013.01); *A61M 2205/75* (2013.01); *A61M 2205/7527* (2013.01)

(58) Field of Classification Search
CPC ...... A61M 2205/7527; A61M 5/14248; A61M 5/145; A61M 5/1684
See application file for complete search history.

(56) References Cited

U.S. PATENT DOCUMENTS

| | | |
|---|---|---|
| 2009/0082757 A1 | 3/2009 | Rogers |
| 2011/0046558 A1 | 2/2011 | Gravesen et al. |
| 2012/0059349 A1* | 3/2012 | Kuo .................... A61M 5/1407 604/500 |
| 2013/0086982 A1* | 4/2013 | Miesel ................ A61M 5/1684 73/149 |

FOREIGN PATENT DOCUMENTS

| | | |
|---|---|---|
| GB | 2 063 071 | 6/1981 |
| WO | WO 02/20073 | 3/2002 |
| WO | WO 2008/100199 | 8/2008 |
| WO | WO 2009/088608 | 7/2009 |
| WO | WO 2009/147478 | 12/2009 |

* cited by examiner

PUMPING DEVICE HAVING IMPROVED EMPTYING DETECTION FEATURES

This application is the U.S. national phase of International Application No. PCT/IB2013/050868 filed 1 Feb. 2013 which designated the U.S. and claims priority to EP 12153541.3 filed 1 Feb. 2012, the entire contents of each of which are hereby incorporated by reference.

FIELD OF THE INVENTION

The present invention relates to containers for fluid substances, e.g. insulin, which are adapted to be fitted to an injection device, such as a pump, which infuses the fluid substance into a patient.

STATE OF THE ART

Infusion pumps, e.g. insulin pumps, have usually a reservoir made of a syringe having a hard shell (see for instance WO 2004/084976 or US 2003/055323). The fluid is contained in a syringe which is has to be pre-filled before the treatment.

Some insulin pumps, such as the one illustrated on FIG. 1, have a rigid cavity 6 defined between a top 3 and bottom 2 hard shell. A pump unit 4 is fixed to the top shell 3. The cavity 6 contains a reservoir which is made of a movable film 1 (e.g. resilient and/or flexible film), such as thermoformed and heat-soldered onto the top shell 3 (see for instance international patent application WO 2007/113708). The bottom hard shell 1 protects the film 2 against external mechanical forces and ensures a water tightness of the system.

The film 1 and the top shell 3 define a reservoir whose volume is variable because of the flexibility of the film. The film is thermoformed to conform to the shape of the cavity when it collapses into the cavity such that the remaining volume is negligible.

The FIG. 1 shows a cross section of disposable part of the device having a film 1, a hard bottom Shell 2, a hard top cover 3, a pump unit, a gasket 5 (tight area) and the reservoir cavity 6.

Before connecting the disposable part as described in FIG. 1 onto the permanent part that contains all the electronics necessary to actuate the pump and communicate via RF to the remote controller, the patient has to fill the reservoir with a syringe via a filling port, e.g. an elastomeric septum located in the top shell 3. The patient also has to enter this volume $V_0$ of insulin into the memory of the remote controller of the pumping device.

This volume information is used to alarm the patient when the difference between $V_0$ and the volume pumped becomes lower than a predefined value, typically 20 Units of insulin (equivalent to 0.2 ml for U100 insulin). This residual volume corresponds to the overnight basal delivery of almost all patients.

The determination of the volume $V_0$ is approximate, typically +/−20 U according to the syringe accuracy (piston diameter, graduation . . . ), the reading accuracy, the filling procedure that includes air bubble removal, the priming volume. Moreover there is a risk of error when the patient enters this volume into the remove controller.

In the patent application WO2010046728 is described a pumping device comprising pressure sensors able to detect dysfunction like reservoir over or under pressure.

By combining the teaching of patent applications WO2010046728 and WO2007113708 there is a possibility to detect the empty reservoir. Since the film is thermoformed to conform to the shape of the cavity when it collapses into the cavity such that the remaining volume is negligible, the relative pressure in the reservoir is small and slightly negative during the complete emptying of the reservoir and suddenly drops dramatically just after the film collapses against the top shell 3. This system can therefore detect an empty reservoir but is unable to detect an intermediate situation, i.e. where a remaining volume of fluid is still present in the reservoir.

The FIG. 14 shows the pressure curve of four distinct reservoirs during their emptying. The reservoir A is an elastomeric reservoir. When the reservoir is made from an elastomeric material, the pressure is usually intended to propel the fluid. This pressure may be also used to deduce which volume is remaining in the reservoir. Indeed, during the emptying and the filling of an elastomeric reservoir, the pressure varies such that a pressure corresponds to a remaining volume. Generally, when the reservoir contains a fluid, the relative pressure in an elastomeric reservoir is positive and during the phase of emptying, it decreases according to the reservoir volume. An alarm may alert the patient when a pressure threshold is reached.

But, when the reservoir pressure varies too much, the pumping accuracy can degrade, and more especially when this pressure is used as propellant. Typical infusion systems are made of a pressurized reservoir, a fluidic restriction and a valve, the delivery accuracy being directly affected by the change of reservoir pressure.

Even for a positive displacement pump, when the pressure is too excessive (negative or positive), the device may deliver the fluid with a poor accuracy. So for an accurate delivery, the reservoir pressure must be as constant as possible.

For the reservoirs B, C and D, the FIG. 14 shows negative pressures but these reservoirs may contain also positive pressures. The reservoir described above typically behave as reservoir B. In this reservoir, even if the pressure decreases slightly, the pressure gradient is so small that the pressure can be considered as substantially constant and its pressure gradient may hardly be detected by a sensor (conversely for an elastomeric reservoir, its pressure gradient is much higher and easily detectable by a sensor). So the reservoir pressure B is substantially constant but when the volume is nearly empty, the pressure drops suddenly. So, when the pressure sensor of the reservoir B can detect a pressure threshold or a predefined pressure gradient, the remains volume is close to zero and it is too late for notifying the patient.

In a medical device such as an insulin pump or a drug delivery device, there is therefore a need for a system that is able to detect when the reservoir still contains a residual volume $V_{res} > 20$ U such that at least 20 U can be delivered with accuracy, independently of the filling volume or patient actions. So the reservoir pressure must be as constant as possible but it must also vary for detecting a remaining volume.

GENERAL DESCRIPTION OF THE INVENTION

The invention is set forth and characterized in the independent claims, while the dependent claims describe other characteristics of the invention.

The present application claims the benefit of the priority of EP 06112066.3 filed on Mar. 31, 2006, PCT/IB2008/054353 filed on Oct. 22, 2008, EP11171155.2 filed on 23, 2011, EP 11172494.4 filed on 4, 2011, EP 12153541.3 filed on Feb. 1, 2011, the entire disclosure of which are incorporated herein by reference.

The present invention offers several improvements with respect to state-of-the-art devices. The present document discloses a reservoir designed to maintain a substantially constant pressure to improve the delivery accuracy of a fluid by for example a delivery device. Furthermore, said reservoir is able to create suitable conditions so that device can detect at least one predefined volume remaining in said reservoir.

In one embodiment, the invention discloses a medical device which can deliver accurately a fluid and can inform the patient of the remaining volume in the reservoir.

In one embodiment, the present invention provides new features for the reservoir design to ensure that a predefined residual volume $V_{res}$ can be infused with accuracy after detection of a predefined pressure gradient and/or a pressure threshold $P_{th}$. These features may be used to inform the patient that the reservoir will soon be depleted.

In one embodiment, the residual volume $V_{res}$ may be comprised between 0.01 ml to 0.5 ml and the threshold pressure $P_{th}$ may be comprised between 5 to 500 mbar. For example, the relative threshold pressure $P_{th}$ may be equal to 50 mbar and the residual volume $V_{res}$ may be equal to 0.2 ml.

LIST OF FIGURES

The invention will be better understood below, with a detailed description including some examples illustrated by the following figures:

FIG. 1 showy a 3D cross section of the disposable part of the device having a film 1, a hard Bottom Shell 2, a hard top cover 3, a pumping unit 4, a gasket 5 (tight area) and the reservoir cavity 6.

Figure 6:
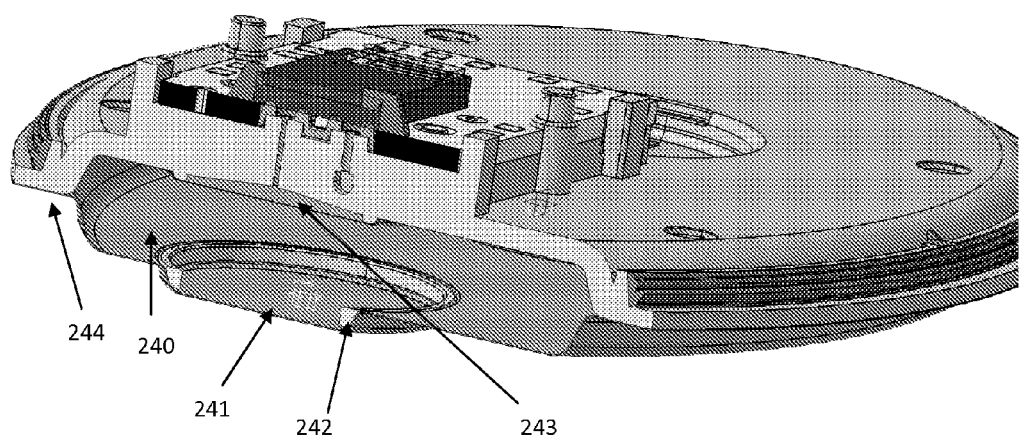

FIG. 6 discloses an example of ring attached to the film for improved empty reservoir detection.

Figure 7:
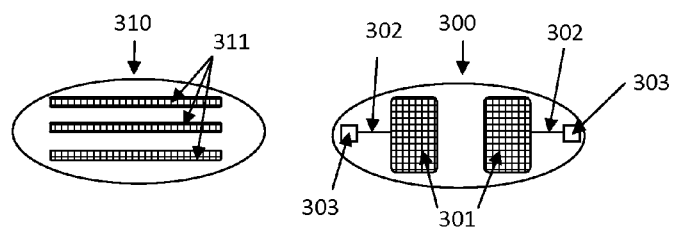

FIG. 7 shows two distinct parts of the device comprising conductive areas

Figure 8A:
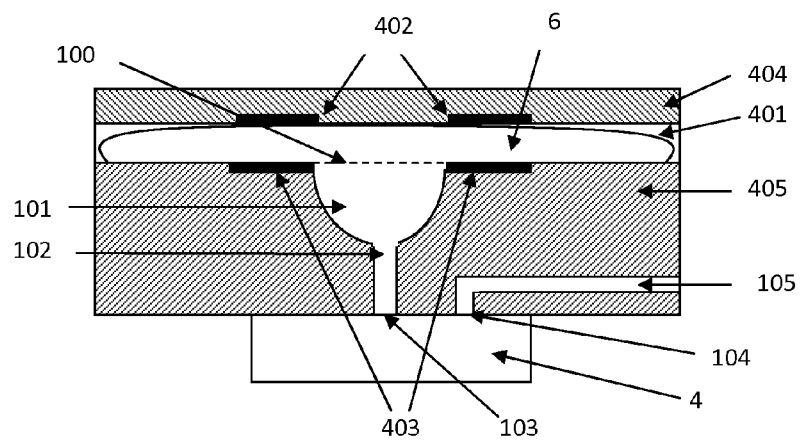
Figure 8B:
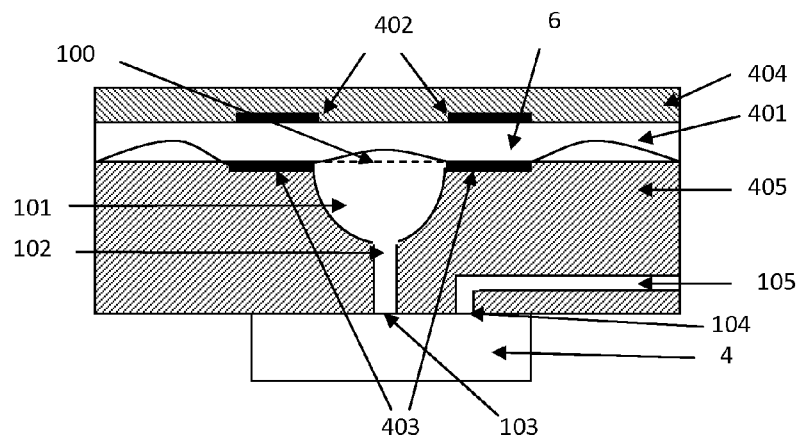

FIGS. 8 and 8b discloses a device comprising magnets on both top and bottom shell.

Figure 9A:
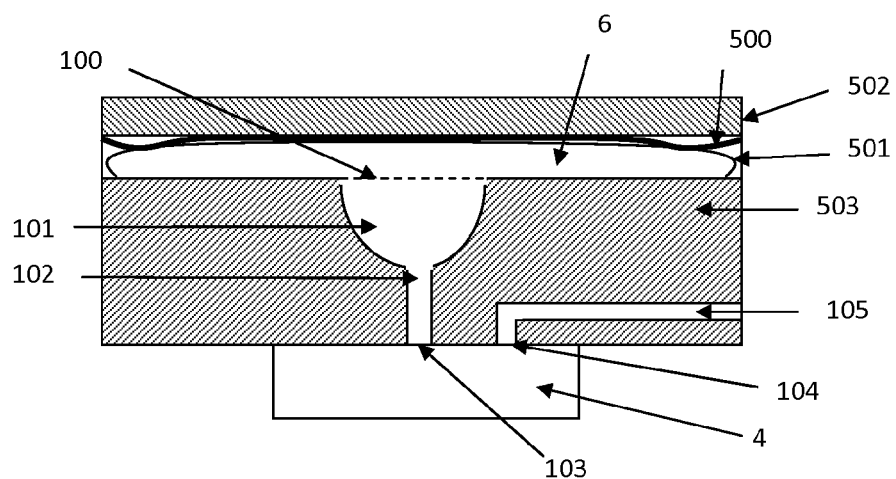
Figure 9B:
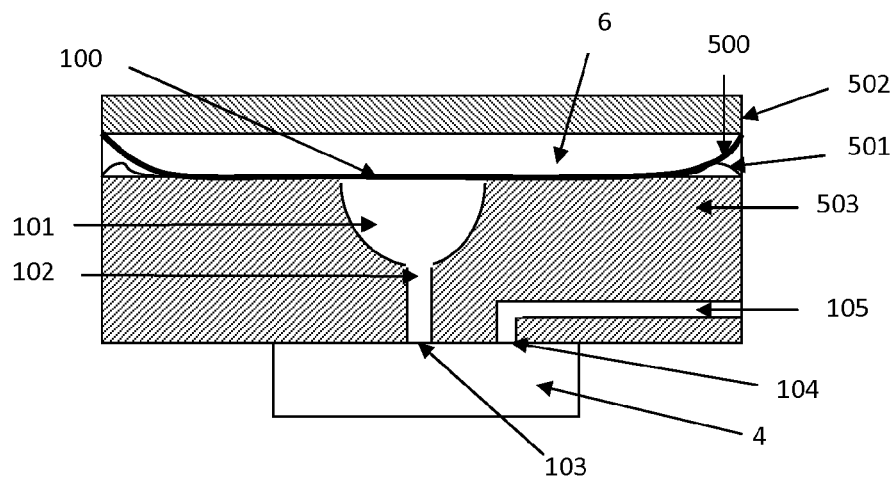
Figure 9C:
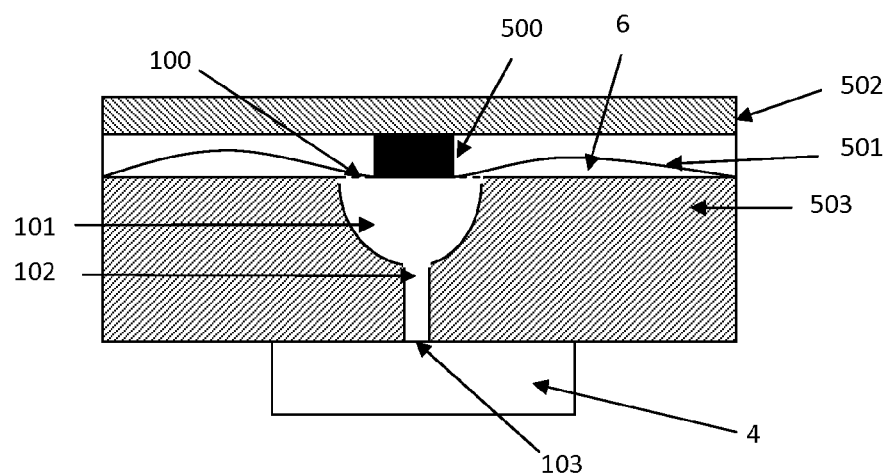

FIGS. 9a and 9b show across-section of a device comprising a thin sping attached to the film FIG. 9c is the view at 90° of the cross-section of a device shown in FIG. 9b comprising a thin sping attached to the film in case of a reservoir partially empty (sping in a second position).

Figure 12A:
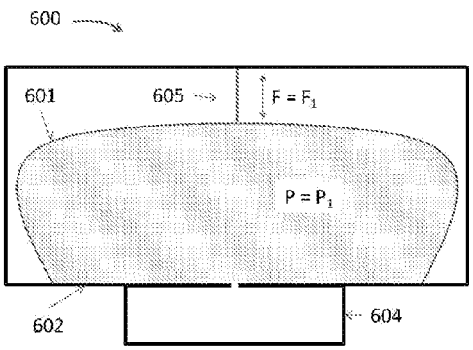
Figure 12D:
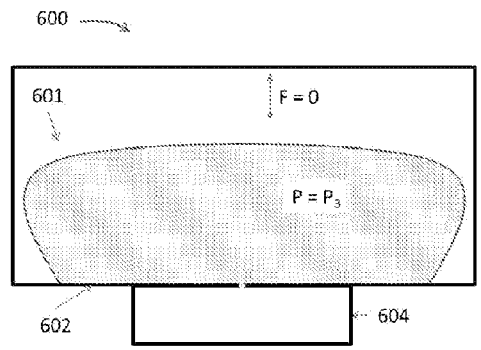
Figure 12B:
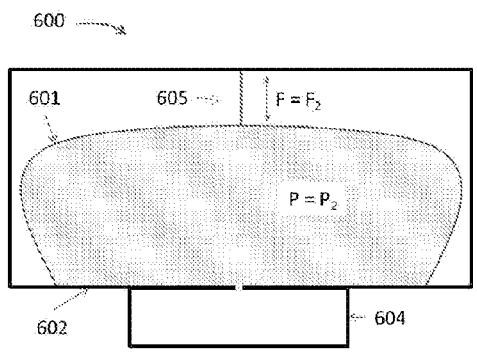
Figure 12E:
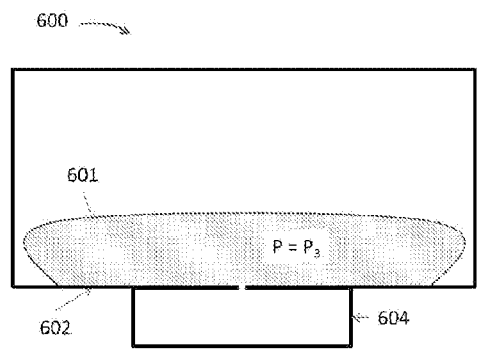
Figure 12C:
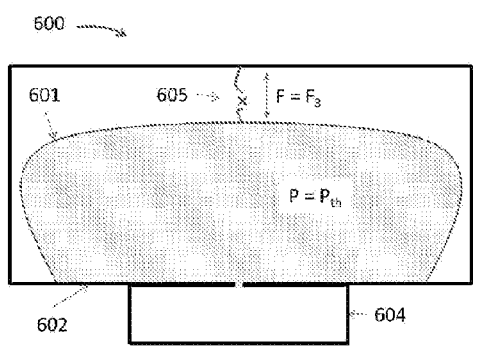
Figure 12F:
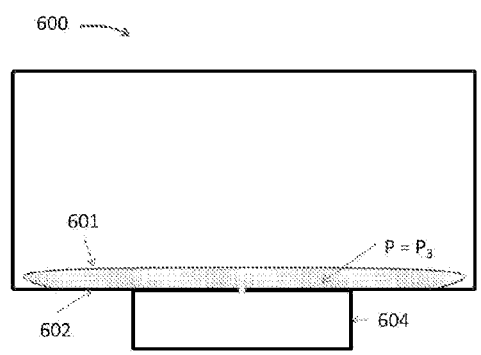
Figure 12G:
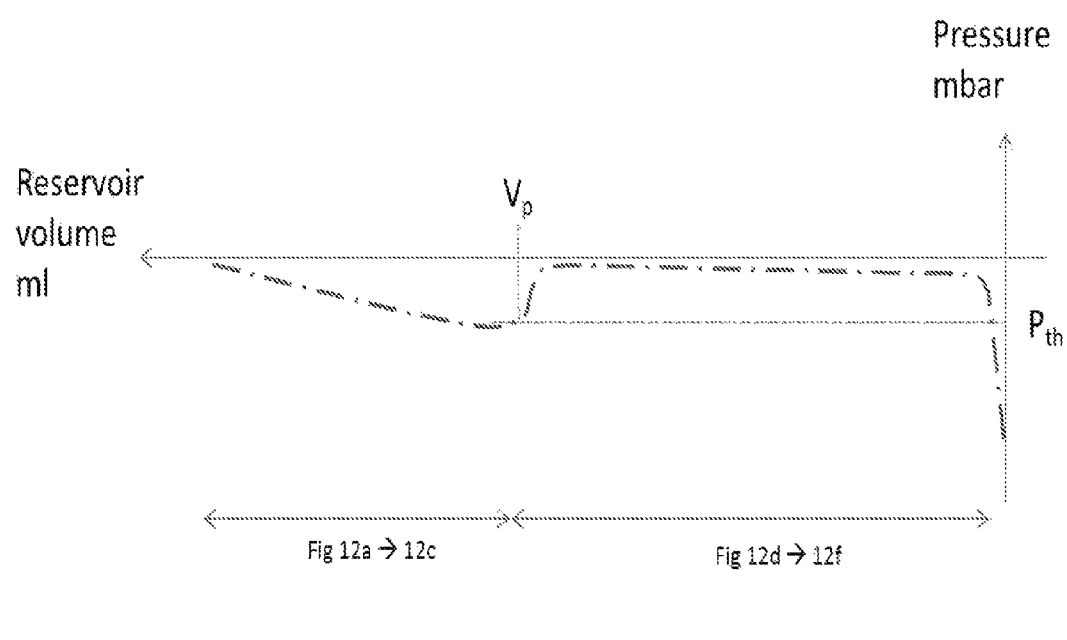
Figure 13A:
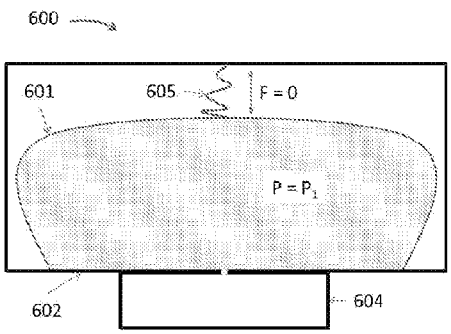
Figure 13D:
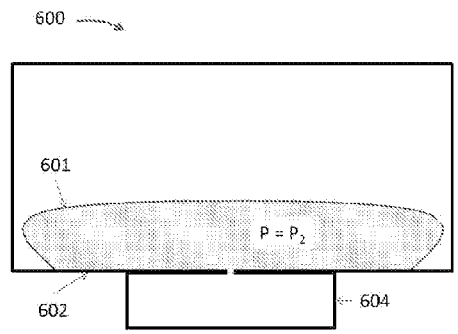
Figure 13B:
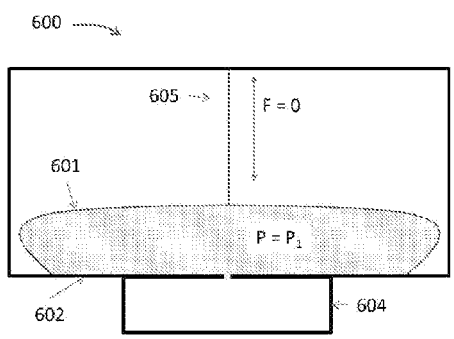
Figure 13E:
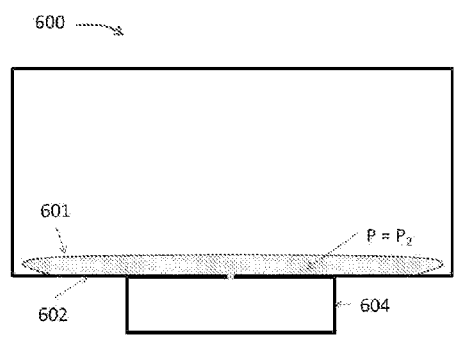
Figure 13C:
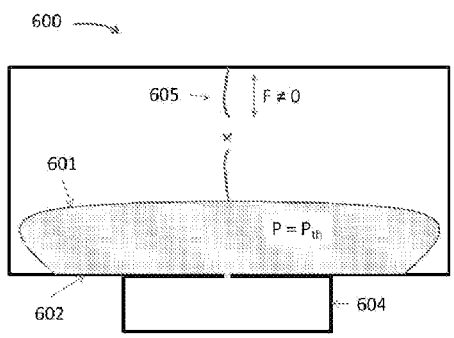
Figure 13F:
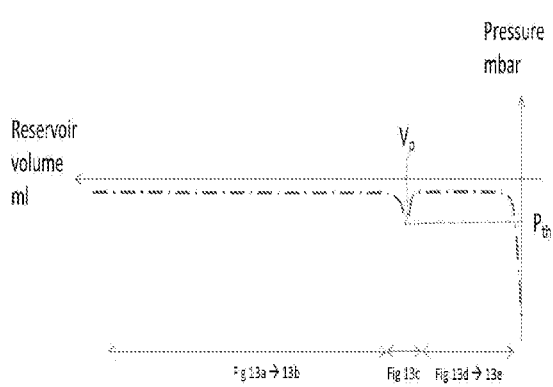
Figure 14:
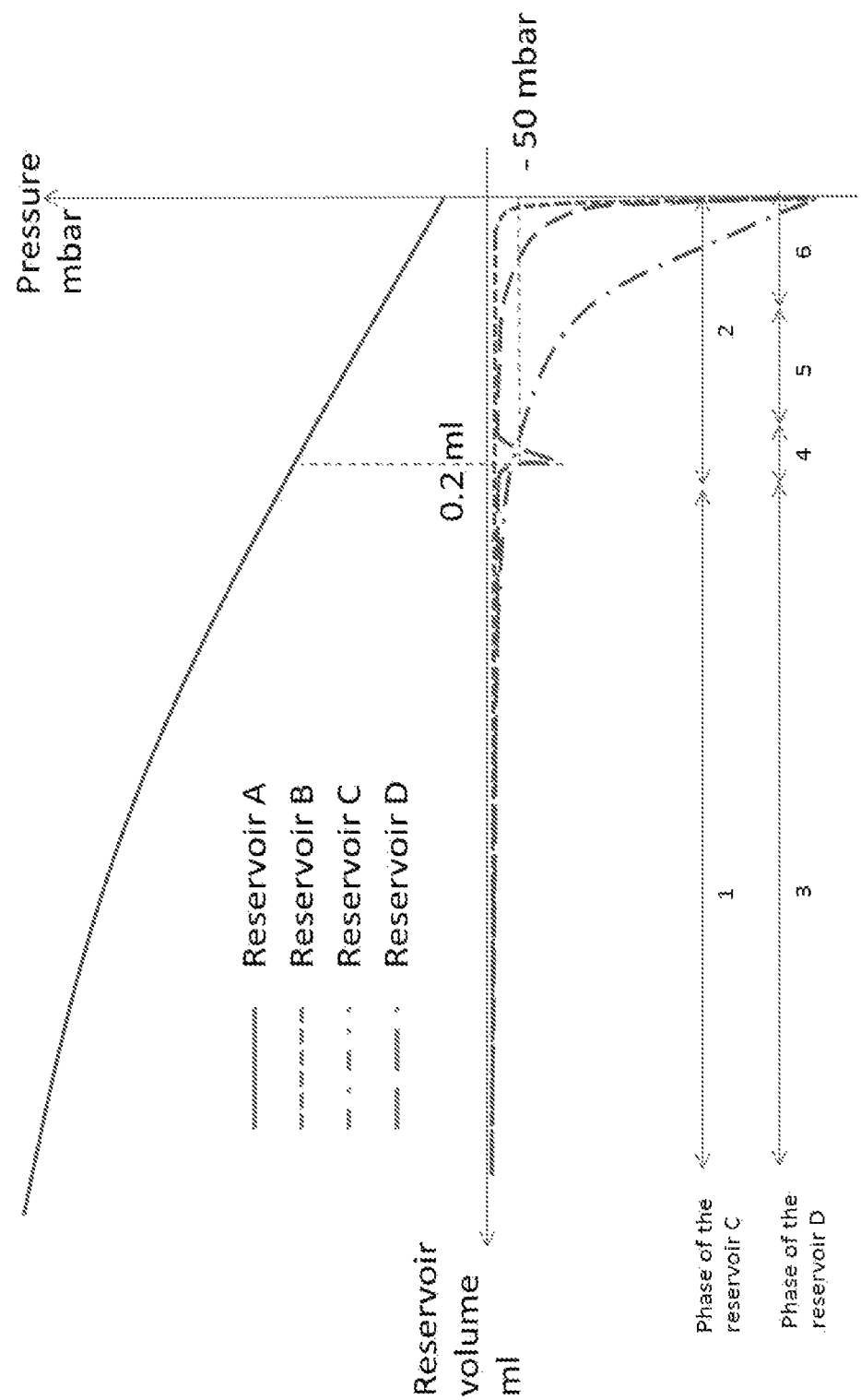

FIGS. 10a to 10f schematise the emptying of the device comprising an elastic means FIGS. 11a to 11f schematise the emptying of the device comprising a cavity FIGS. 12a to 12g schematise the emptying of the device comprising a temporary biasing means FIGS. 13a to 13f schematise the emptying of the device comprising another temporary biasing means FIG. 14 shows the pressure in the four distinct reservoirs during the emptying

DETAILED DESCRIPTION OF THE INVENTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and/orientations.

As used in this specification and the appended claims, the term "or" is generally employed in its sense including "and/or" unless the content clearly dictates otherwise.

The present document discloses a reservoir which may be used in a medical device. Said reservoir may insure a substantially constant pressure as long as possible in such a manner as to permit an accurate delivery by for example a medical device.

Furthermore, said reservoir may change its behaviour. For example, said change may occur at a predefined volume so that it would be possible to deduce the remaining volume in the reservoir when said reservoir behaviour changes.

By the term "reservoir", it should be understood all elements permitting to contain securely a fluid, which will be injected, and to create suitable conditions so that a device can deliver with accurate and detect a predetermined volume remaining in said reservoir. Said reservoir may comprise rigid and/or flexible walls and at least one access port which communicates with the interior of the reservoir. In one embodiment, said access port may be an outlet and/or an inlet. In another embodiment, the reservoir may comprise two distinct access ports which may be an inlet and an outlet.

In a preferred embodiment, said reservoir comprises a biasing means. Said biasing means may exert at least temporarily a force called "biasing force" on the reservoir or on one of the reservoir wall in such a way as to change the reservoir behaviour. In one embodiment, said behaviour change may induce a variation of the reservoir pressure up to a predefined pressure gradient and/or pressure threshold such that, for example, a pressure sensor can detect said predefined pressure gradient and/or pressure threshold. In one embodiment, said biasing means may be a specific design of the reservoir wall and/or another element. In the present document, the reservoir pressure is the fluid pressure in the reservoir.

By the term "behaviour change", it should be understood that the reservoir may have at least two distinct behaviours. In the state of art, the document explains that the reservoir pressure must not vary the reservoir pressure for insuring an accurate delivery but if the reservoir pressure does not vary it's difficult to know the remaining volume contained in said reservoir. So this invention discloses a new reservoir design. Said reservoir can change its behaviour at a predefined state of the reservoir. In particular, in this document, the invention uses said behaviour change (which can be detected and/or acknowledged) at a predefined volume so as to know the remaining volume when said change occurs. However, the invention is not intended to be limiting at a behaviour change of a reservoir so as to know a remaining volume.

In one embodiment, said biasing means causes, at least temporarily, at least one behaviour change for inducing at least one variation of the reservoir pressure up to a pressure threshold and/or a predefined pressure gradient which may be detected by a pressure sensor. So thanks to said biasing means which causes said behaviour change, the emptying and/or the filling of said reservoir may comprise several phases, in particular two distinct phases: a constant phase and a variable phase. Each phase may be temporary but, the constant phase should preferably be longer than the variable phase. A constant phase may be followed by a variable phase and/or vice versa. During the emptying and/or the filling, several constant phases and several variable phases could be combined.

In said embodiment, each phase is characterised by a pressure curve of the fluid contained in the reservoir. The constant phase is characterised by the fact that the reservoir pressure is substantially constant. In other term, during a constant phase said biasing means does not exert any biasing force on the reservoir. By the term "substantially constant", it should be understood that, during the constant phase, thanks to reservoir design, the reservoir does not create any over or under pressure to the fluid and the reservoir volume varies depending on the volume of the fluid contained in said reservoir. So, the reservoir pressure varies only marginally. In one embodiment, the reservoir pressure is equal or slightly smaller than an external pressure.

Conversely, the variable phase is characterised by the fact that the reservoir pressure varies. In other term, during the variable phase, the biasing means may exert a biasing force inducing a variation of the reservoir pressure. In one embodiment, the reservoir pressure is smaller than an external pressure.

In one embodiment, the reservoir pressure may depend on the external environment.

In one embodiment, the invention discloses a medical device for delivering a fluid. Said medical device comprises a collapsible reservoir as described by this invention, a pressure sensor, a pumping system in communication with said reservoir through said access port. Said pressure sensor is operable to detect a pressure threshold or a predefined pressure gradient of the fluid contained in the reservoir. So, when a predefined volume is reached, the reservoir behaviour changes causing a variation of the reservoir pressure up to said pressure threshold or said predefined pressure gradient. When the pressure sensor detects said pressure threshold or said predefined pressure gradient, the medical device can deduce that the volume remaining in the reservoir is the predefined volume. In other term, the biasing means exerts a biasing force at least temporarily on said reservoir so as to change at least temporarily its behaviour at a predefined volume. Said behaviour change induce a variation of the reservoir pressure which is detected by the pressure sensor such as the medical device can know the remaining volume In one embodiment, said pressure threshold and/or said predefined pressure gradient is reached suddenly and/or is significant compared, for example, with the pressure during the constant phase.

In one embodiment, the reservoir can change several time its behaviour so as to determine several predefined volumes.

In one embodiment, a remaining volume may be a residual volume $V_{res}$. Said residual volume $V_{res}$ corresponds to a safety volume sufficient to ensure a safety margin to alert the user before the reservoir is empty. In one embodiment, the medical device may be an insulin delivery device. Said residual fluid volume may be 0.2 ml, so said volume may correspond to 20 units of insulin In one embodiment, during pumping, the reservoir film 1 collapses progressively onto the hard shell 3 that contains the filter. The under pressure is ideally limited to only few millibars during almost all the emptying of the reservoir. This under pressure is due to the small attractive force of the film (for thin and resilient film) onto the fluid. When the reservoir film 1 collapses onto the top shell 3 that contains a filter, a large under pressure is generated and after detection by the integrated pressure detector, the state of the art device allows the additional injection of only few units with accuracy, because the residual volume is small by design and because the pump stroke is incomplete in case of large reservoir under pressure.

In one embodiment, the system is designed to generate, when the reservoir is not completely empty, a reservoir under pressure $P_{th}$ that could be detected by a sensor, and to ensure that the residual volume $V_{res}$ that can be pumped with accuracy is larger than a predefined value.

The term "reservoir under pressure $P_{th}$" may be understood as a negative relative pressure equal to a difference between the pressure inside and outside the reservoir.

The sensor may be a relative pressure sensor (gauge). The value of the pressure sensor and the predefined value as threshold pressure or reference pressure are therefore relative.

The FIGS. 10, 11, 12 and 13 schematise the distinct phases of the emptying of the reservoir using different means to change the behaviour of the reservoir. These figures do not disclose particular embodiments but explain conceptually how different reservoirs and its biasing mean work.

Figure 10A:
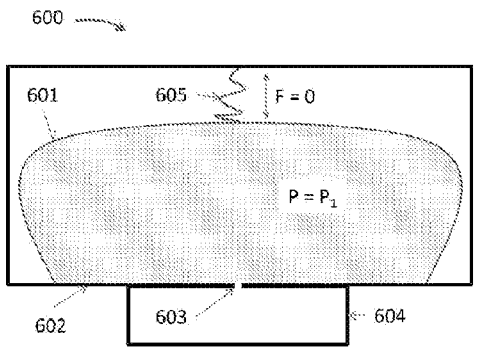
Figure 10D:
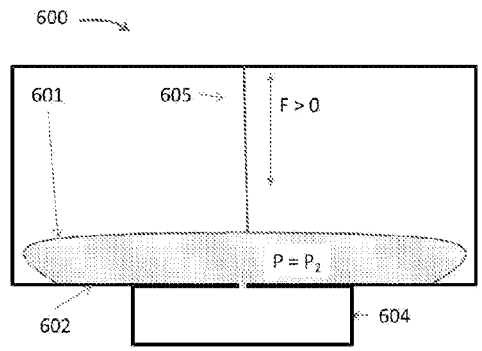
Figure 10B:
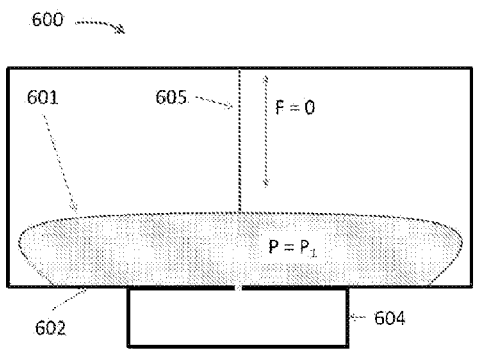
Figure 10E:
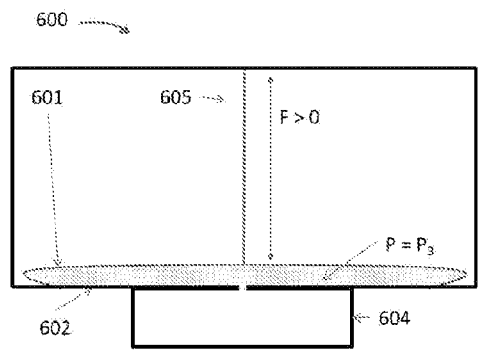
Figure 10C:
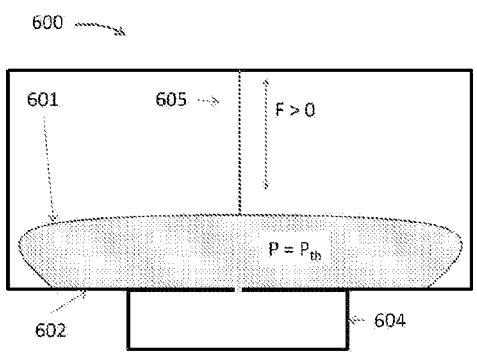
Figure 10F:
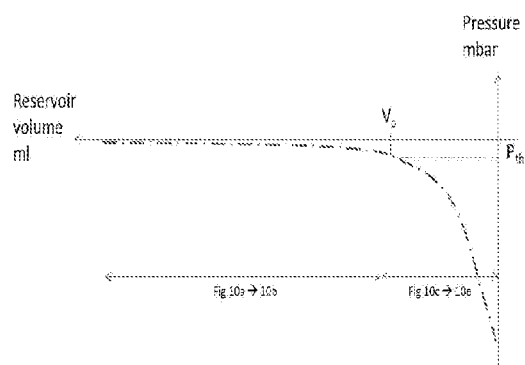

The FIGS. 10a to 10e show a device which comprises a reservoir 600 and a pumping system 604. Said reservoir 600 comprises a flexible wall 601, a rigid wall 602, an access port 603 and a biasing means 605 which may exert at least temporarily a biasing force on the wall 601. The FIG. 10f shows the curve of the reservoir pressure of said device. Said biasing means may be means as a rubber band and may be sufficiently long to no exert any biasing force on the wall 601 before a predefined volume of the reservoir is reached. In the FIG. 10c, the reservoir reaches a predefined volume $V_p$ (which may be a residual volume), so the reservoir behaviour changes thanks to said biasing means 605. So, the pressure P reaches a pressure threshold $P_{th}$ or a predefined pressure gradient which is detected by a pressure sensor (not represented here). In the FIGS. 10d and 10e, the biasing means 605 increase its biasing force such as to vary the pressure P. Here, P1 may be equal or slightly smaller than the external pressure. P1 may be higher than P2 which may be higher than P3. The FIGS. 10a and 10b correspond to a constant phase where the pressure P of the fluid contained in the reservoir is substantially constant and equal to P1. The FIGS. 10c, 10d and 10e show a variable phase.

Figure 11A:
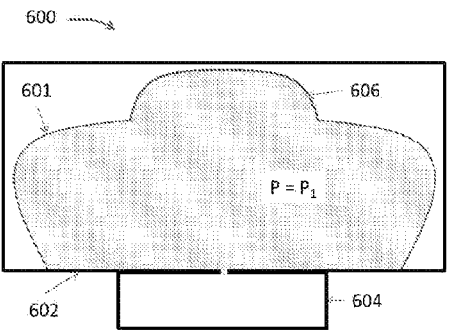
Figure 11D:
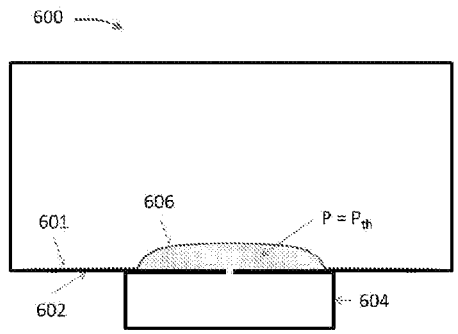
Figure 11B:
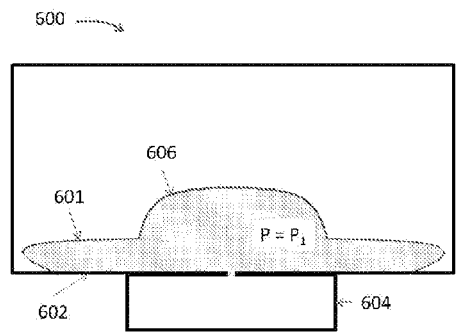
Figure 11E:
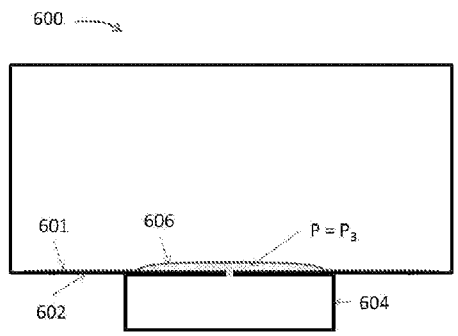
Figure 11C:
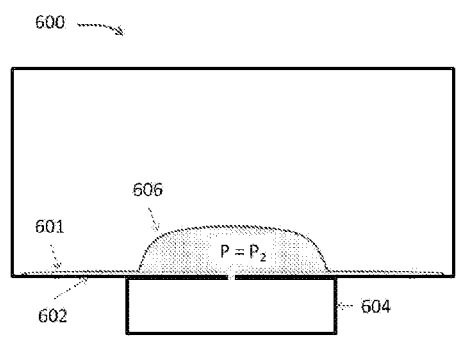
Figure 11F:
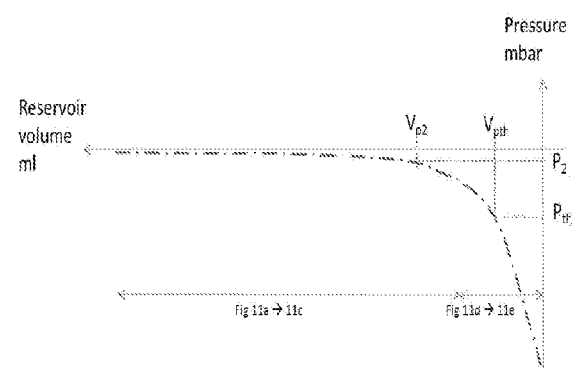

The FIGS. 11a to 11e show a device which comprises a reservoir 600 and a pumping system 604. Said reservoir 600 comprises a flexible wall 601, a rigid wall 602, an access port and a biasing means 606 which may exert at least temporarily a biasing force on the wall 601. The FIG. 11f shows the curve of the reservoir pressure of said device. The biasing means is a specific design (material and/or form and/or other) of the wall 601. Here, the biasing means 606 may be a cavity which may contain a predefined volume. Said biasing means does not exert any biasing force on the wall 601 before the volume of the reservoir is equal to said predefined volume. Said cavity may be designed in the rigid wall 602. In the FIG. 11c, the reservoir is close to the predefined volume, so the reservoir behaviour changes thanks to said biasing means 606. The pressure P decreases up to P2. Here, said behaviour change is more gradual and the pressure $P_{th}$ has not yet been reached. In the FIG. 11d, the pressure P reaches a pressure threshold $P_{th}$ or a predefined pressure gradient which is detected by a pressure sensor (not represented here). In the FIGS. 11d and 11e, the biasing means 606 increase its biasing force such as to vary the pressure P. Here, P1 may be equal or slightly smaller than the external pressure. P1 may be higher than P2 which may be higher than P3. The FIGS. 11a and 11b correspond to a constant phase where the pressure P of the fluid contained in the reservoir is substantially constant and equal to P1. The FIGS. 11c, 11d and 11e show a variable phase. Here, the behaviour change occurs before the pressure P has reached the pressure threshold $P_{th}$ and/or the predefined pressure gradient. So, the reservoir may have two distinct predefined volumes $V_{pth}$ and $V_{p2}$. And, the device may notify two distinct alerts corresponding on two distinct volumes remaining in the reservoir: alert 1: "The reservoir contains only XX ml", alert 2: "The reservoir is nearly empty!!!".

The FIGS. 12a to 12e show a device which comprises a reservoir 600 and a pumping system 604. Said reservoir 600 comprises a flexible wall 601, a rigid wall 602, an access port and a biasing means 605 which may exert at least temporarily a biasing force on the wall 601. The FIG. 12g shows the curve of the reservoir pressure of said device. The biasing means may exert a biasing force when the reservoir is full or nearly full. Here, the biasing means 605 may be a means being characterised by a determined length and a relative fragility. So, said biasing means 605 may withstand up to a biasing force F3 which corresponds to the force generate by the reservoir when the reservoir pressure has reached the pressure threshold. When, as showed in FIG. 12c, the biasing force is equal or higher than F3, the biasing means 605 becomes disabled so that, in FIGS. 12d, 12e and 12f, it does not exert any force on the reservoir. The behaviour change occurs in FIG. 12c. Before, the FIGS. 12a and 12b show a variable phase where the pressure decreases from P1 to $P_{th}$. Then, the FIGS. 12c to 12e, the pressure P is substantially constant and equal to P3 which may be higher than or equal to P1.

The FIGS. 13a to 13e show a device which comprises a reservoir 600 and a pumping system 604. Said reservoir 600 comprises a flexible wall 601, a rigid wall 602, an access port 603 and a biasing means 605 which may exert at least temporarily a biasing force on the wall 601. The FIG. 13f shows the curve of the reservoir pressure of said device. The biasing means 605 may be a means being characterised by a determined length and a relative fragility. Said biasing means is designed to not exert any biasing force on the wall 601 before a predefined volume $V_p$ of the reservoir is reached. In FIG. 13c, when said predefined volume is reached, the reservoir behaviour changes suddenly thanks to said biasing means which exerts a significant biasing force on the reservoir, then the biasing means 605 becomes disabled. So, two behaviour changes have occurred: in FIGS. 13a, 13b, the pressure P is constant and equal to P1; in FIG. 13c the pressure P varies up to a pressure threshold $P_{th}$ or a predefined pressure gradient; then in FIGS. 13d et 13e, the pressure P is constant and equal to P2. P1 may be equal to P2.

In one embodiment, the reservoir comprises several and/or distinct biasing means.

The FIG. 14 shows the graph for comparing the behaviours of distinct reservoirs. The reservoir A is a classical reservoir which may made of elastomer, its behaviour does not change. The reservoir B is a reservoir as described by the application patent WO 2007/113708. Said reservoir comprises a collapsible wall and its pressure is substantially constant but when the fluid volume is close to 0, the reservoir pressure drops suddenly. The reservoir C and D are two distinct embodiments of this invention. Both maintain a substantially constant pressure as long as possible and both are operable to change this behaviour when the fluid volume reaches a predefined fluid volume so that the pressure sensor can detect this change and notify the patient. The reservoir C has only two distinct phases, a first phase (1) which is a constant phase followed by the second (2) which is a variable phase. The reservoir D comprises severable phases. The first phase (3) is a constant phase then a biasing means causes a first behaviour. Said behaviour is suddenly and sufficiently significant for generate a reservoir pressure up to a pressure threshold and/or a predefined pressure gradient. Said behaviour causes temporarily a variable phase (4) followed by a new constant phase (5). Before the reservoir is empty, other behaviour occurs and induce a final variable phase (6).

Several proposals are provided hereafter, including the design of a cavity below the filter, the structuration/thermoforming of the reservoir film, the use of electric solution to detect the collapse, the use of magnets or mechanical means to generate the under pressure necessary for the detection and then to release the pressure after detection. In the present document, the values of pressure and/or volume and/or other are given for example. The device is not limited to said values.

Filter Cavity

Figure 1:
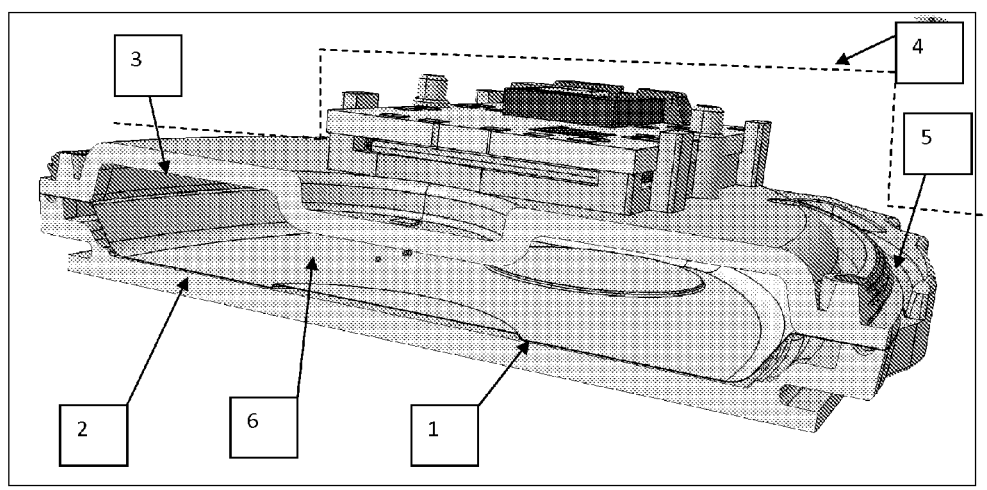
Figure 2A:
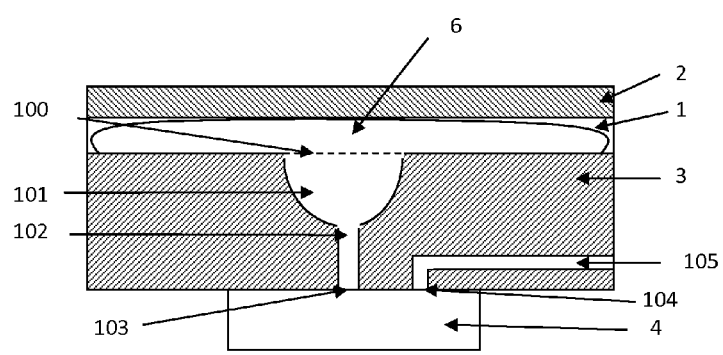
FIGS. 2a to 2b show a cross-section of the device comprising a cavity and a filter

In a first embodiment of the present invention the top shell 3 includes a filter 100 (dashed line in FIGS. 2a and 2b) having a cavity 101 underneath which communicates via a channel 102 with the inlet 103 of the pumping unit 4 as shown in FIG. 2a for a filled reservoir 6. The outlet 104 of the pumping unit is connected to a fluidic pathway including a channel 105 and other components not represented here like a cannula.

Figure 2B:
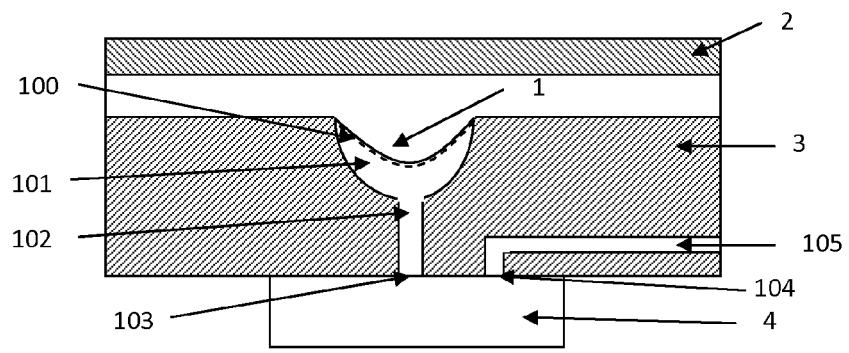

The reservoir 6, when filled with a fluid, lifts the film 1 (plain line in FIGS. 2a and 2b) against the bottom shell 2 which is therefore a mechanical stopper for the deflection of the film 1. When the fluid contained in the reservoir 6 is completely pumped, the film 1 will collapse on the top shell 3 and the filter 100. At this stage the filter cavity 101 is still filled of fluid. The pumping unit will generate an under pressure in the filter cavity and therefore will deflect both film and filter as shown in FIG. 2b.

The volume of the filter cavity 101 is therefore a buffer that will be pumped when the reservoir 6 is empty by deforming the film and the filter itself, inducing an under pressure that shall be detected by the integrated sensor in the pump. This under pressure is progressive thanks to the elasticity of the filter and the reservoir film. The final volume of fluid that could be extracted with accuracy (i.e. without loss of the pumping accuracy) after detection of the under pressure threshold (that triggers an alarm) is therefore well controlled.

Additional features could be implemented in the filter cavity 101 to improve the generation of the under pressure $P_{th}$, e.g. the use of texturing or stripes or corrugations or any structures into the cavity will make more difficult the collapse of the filter, inducing a faster detection of the empty reservoir.

The presence of a pillar in the filter cavity 101 will limit the deflection of the filter 100 and reduce its elasticity, inducing a faster increase of the under pressure during the reservoir emptying.

The pillar or any other feature in the filter cavity may be attached to the filter itself, e.g. by thermowelding, ultrasonic welding, gluing or any other means. A filter frame (like a net with openings of any shape) should be attached to the filter before assembly or directly machined or molded in the cavity of the top shell and attached to the filter during assembly by any means. From the original filter membrane having a large dimension up to several centimeters it results, after assembly with the frame, in the creation of several smaller filters with therefore higher rigidity.

The filter 100 is preferably a polymeric hydrophilic membrane with micrometric or sub-micrometric pore size. The density of the pores, the thickness and the surface of the filter membrane are designed to ensure that the fluidic resistance of the filter is small compared the pump itself.

Typical membrane thickness is few tenths to few hundredths of microns.

Typical pore density varies from 1% to more than 25% of the total filter surface.

The filter 100 is intended to prevent particle and insulin fibrils contamination and to block air present in the reservoir. The patients are trained to remove air from the reservoir during the filling but the presence of residual bubbles cannot be excluded.

The presence of air in the reservoir including the filter cavity has an effect on the detection sensitivity of the empty reservoir, on the residual pressure in the reservoir during filling, on also the effective quantity of fluid present in the pump after priming. The quantity of air in the reservoir shall be therefore minimized by design or by specific actions.

The surface of the filter should be large enough to prevent the blocking due to large bubbles.

This filter cavity 101 is designed to ensure perfect priming without air trapped below the filter. The cavity has therefore a small slope that allows a progressive wetting of the cavity surface. The shape of the cavity is moreover slightly conical to drain the residual bubbles towards the hole in the top shell.

Hydrophilic materials, hydrophilic coating or treatments are used to improve the wettability of the filter cavity.

To minimize the volume of air trapped in the reservoir 6 and the filter cavity 101, the reservoir is either collapsed in production with vacuum or directly by the patient itself, before the filling process: the pump is simply actuated and the residual air is pumped. The volume of air in the reservoir depends on the geometry of the reservoir as well as the compression ratio of the pump. A relative pressure of −500 mbar is typically obtained in the reservoir when the pump is actuated without fluid (before filling). The volume of the residual air, after release of this under pressure by the filling, is therefore decreased by the method.

The residual air in both filter cavity and reservoir could be purged just before the filling by the patient himself using a syringe and a needle plugged into the filling port. The under pressure generated by this manual emptying is controlled by the placing the syringe piston in a predefined position, e.g. at the middle of the syringe range (for a 5 ml syringe scale, the rubber piston should be placed at the graduation 2.5 ml). The maximum under pressure in the reservoir and the cavity filter is 500 mbar (for example) in the latter case, when the patient pulls completely the syringe piston.

Reservoir Film Structuring

The same principle of texturing or corrugating or any other means to generated protrusions could be applied not only on the filter cavity but also on the reservoir film 1 and/or on the hard shell 3 of the reservoir and/or on the filter 100 itself.

The goal of the features is again to generate the under pressure $P_{th}$ that triggers an low reservoir alarm while the residual volume $V_{res}$ is still larger than a predefined quantity, for example 20 units of insulin or 0.2 ml.

The design of the reservoir could also include draining features (grooves in the hard shell of the reservoir). The reservoir film is structured (e.g. thermoformed) in such a way that it does not fit perfectly with the hard shell. This asymmetry between the hard shell and the film will make more difficult the collapse of the film and therefore increase $V_{res}$.

In case of a structuration of the hard shell only: no buckling of the reservoir film is expected and the reservoir pressure decreases progressively.

Figure 3A:
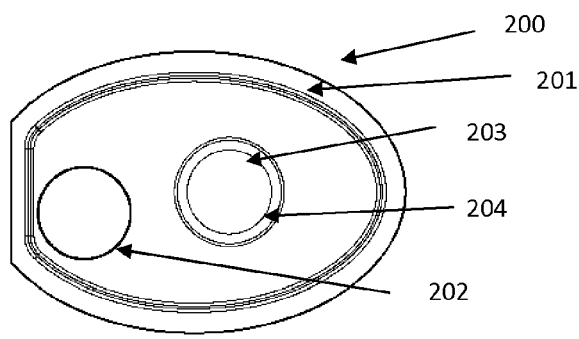
FIGS. 3a and 3b show a view of a thermoformed film showing a shallow protrusion (bump), a protrusion with rigid ring or spacer and a honeycomb-like structuration.

The FIG. 3a illustrates as a non-limiting example of the present invention a thermoformed film 200 having a bonding area 201 which is intended to be bonded to the top shell 3, a shallow protrusion 202 (bump) and a larger protrusion 203 with a rigid ring (spacer) 204.

Figure 3B:
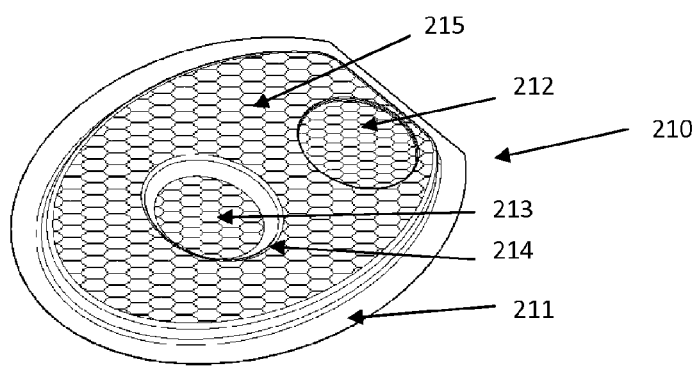

The FIG. 3b illustrates as non-limiting example of the present invention another thermoformed film 210 having a bonding area 211, a shallow protrusion 212 (bump), a larger protrusion 213 with a rigid ring 214 and a honeycomb-like structuration 215 over the film surface, excepted bonding areas.

In case of a structuration/thermoforming of the film or the filter only, the buckling effect of the structured part of the film (e.g. a circular bump) will generate the under pressure $P_{th}$, and just after buckling the under pressure is reduced, making easier the pumping of the residual volume.

In case of a structuration of both hard shell and reservoir film (e.g. the film is thermowelded onto the top shell and assembled after a flip of the film, a top shell cavity facing a bump), the same buckling effect will induce a larger residual volume. The bump will be distorted by the under pressure in the reservoir and will fit to the facing top shell cavity after a complete buckling of the film.

Figure 4:
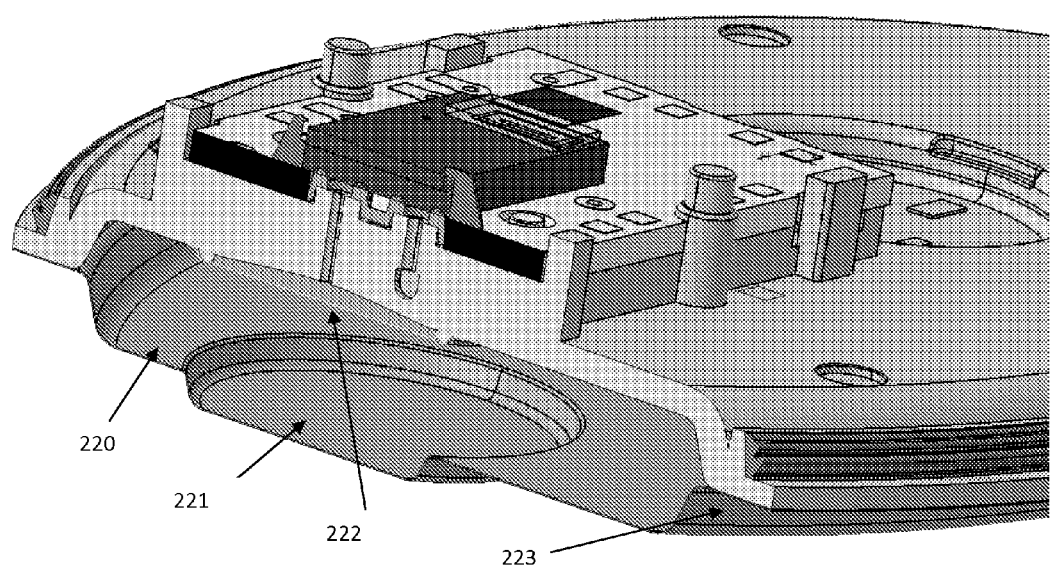
FIG. 4 shows a device comprising a thermoformed film having a protrusion in front of the filter.

An example of thermoformed film 220, with bonging area 223, having a protrusion 221 in front of the filter 222 is shown FIG. 4.

To generate the under pressure $P_{th}$ it is possible to adjust the dimension and the shape of the structure in the film and/or in the hard shell. The properties of the film material could be also adapted accordingly (thickness, rigidity . . . ).

Figure 5:
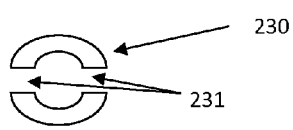
FIG. 5 is the top view of a half-ring like spacer with openings to allow fluid drainage after contact with the top shell.

A rigid or semi-rigid spacer 230 having advantageously lateral openings 231 as shown in FIG. 5 may be attached to the film, the inner volume of the spacer being for instance larger than $V_{res}$. When the spacer comes into contact with the hard shell 3, this residual volume $V_{res}$ is pumped while the film above the spacer is attracted toward the hard shell, generating a negative pressure that can be detected. After contact, the fluid flows through the lateral openings 231.

The FIG. 6 shows, as a non-limiting example of the present invention, a spacer 242 attached to the film 240 (having bonding areas 244) inside a protrusion 241, said ring being placed in front of the filter 243.

Electrical Solution

In another embodiment of the present invention, the reservoir film includes conductive areas on its surface opposite to the one in contact with the fluid. This conductive area closes an electrical circuit located in the bottom shell during the filling. The collapse of the film against the top shell when the reservoir is empty opens the electrical circuit when the residual volume becomes smaller than a predefined value.

As non-limiting example, a bottom shell 300 having two electrodes 301 connected to contact pads 303 via leads 302 is shown FIG. 7 (right). When the bottom shell 300 is assembled to the pumping unit, the two pads are connected electrically to an electronic circuit (not represented here) able to detect the shortage between the two electrodes.

The external surface of the transparent or translucent film 310 is here partly metalized (metallic layers 311) to make the contact while there are still transparent or translucent areas in between to allow the observation of bubbles during priming as illustrated in FIG. 7 (left).

The inner part of the reservoir should be protected against water ingress.

This embodiment of the present invention allows the system to detect when the amount of insulin inserted in the reservoir is large enough to make possible the emptying detection.

Magnet

In another embodiment of the present invention, a magnet is located in the bottom shell or in the patch and pulls thin ferromagnetic (e.g. iron) part glued or deposited onto the film. During the filling this ferromagnetic area on the film comes in contact with the bottom shell. The pulling force shall be able to withstand an under pressure of 50 mbar (for example) below the film. Once this under pressure is generated by the pumping unit in the reservoir, the film can collapse over its whole area including the ferromagnetic area, and the residual volume shall be larger than 20 U (for example) when $P_{th}$ is reached.

In another embodiment of the present invention, the device includes at least two magnets, e.g. a first one located in the bottom shell and a second one located in the hard shell of the reservoir or directly in the permanent part. The second magnet is used to release the negative pressure in the reservoir after detection.

The FIG. 8a illustrates, as a non-limiting example of the present invention, a device with the reservoir 6 completely filled with fluid and having magnets 402 located in the bottom shell 404 and magnets 403 in the top shell 405, the film 401 being coating or covered with a ferromagnetic layer.

During the filling, a ferromagnetic area on the film is first attracted by the magnet of the bottom shell. After pumping a predefined volume, the film pulls the fluid and generates an under pressure of 50 mbar (for example) up to the complete separation between the film and the bottom shell. Then the ferromagnetic area of the film comes into contact with the hard shell of the reservoir in such a way that there is no overpressure generated during this movement in the reservoir. By using these two magnets, there is a possibility to generate an under pressure, when the reservoir is in its first stable position, which can be detected by the inner detector, and to release this under pressure when the reservoir goes toward its second stable position, ensuring an accurate infusion.

The positions and/or the shape of the magnets and/or the shape of the ferromagnetic area of the film should ensure a drainage of the residual volume with accuracy, e.g. the use of magnets having half-ring shape (as illustrated in FIG. 5 for the spacer) or the use of only one magnet would allow the drainage of the residual fluid when the ferromagnetic film 401 comes in contact with the magnet(s) 403 of the top shell 405.

Mechanical Solution/Bi-Stable Film

In another embodiment of the present invention a bi-stable film is obtained mechanically without magnets.

Any other methods to attach the reservoir film onto the bottom shell can be used to that end.

The bottom shell can include a flexible part (e.g. hair clip or a double-bar spring like bi-stable systems) that is attached to the reservoir film. When the film is pulled down during infusion, this flexible part is bended, inducing a restoring force onto the film. The restoring force is such that an under pressure $P_{th}$=50 mbar (for example) induces a deflection of this part such that there is still 20 U (for example) to be infused towards the patient with accuracy.

Ideally, this flexible part has two stable positions (e.g. buckled sping having the two ends attached) the under pressure necessary to switch from one position to the second one being 50 mbar.

In that later case, the residual volume $V_{res}$ should be repeatable. This volume can be much larger than 20 units or 0.2 ml (for example) because it becomes possible to determine the limit of 20 units (for example) when the difference between $V_{res}$ and the pumped volume after detection is 20 units (for example).

The FIG. 9a illustrates, as a non-limiting example of the present invention, a thin hair clip like sping 500 in a first position, said sping being attached to the film 501 and to the bottom shell 502 or the top shell 503. The sping has two stable positions against the top shell 503 (first position) and against the bottom shell 502 (second position) respectively. The reservoir 6 is here completely filled with fluid. After a predefined number of actuations, the under pressure generated by the pumping unit in the reservoir is enough to pull the sping which recovers its original shape (its shape before the filling when the sping is in the second position) against the top shell 503 as illustrated in FIG. 9b. The dimension of the sping and the shape of the film 501 are both designed to prevent any overpressure in the reservoir 6 during this movement of the thin sping 500. The FIG. 9c illustrates, with a view at 90° with respect to the cross-section depicted in FIG. 9b, the shape of the film 501 after the change of the sping position and the amount of the residual volume $V_{res}$ of the reservoir 6 that can still be pumped. Only the part of the film 501 attached to the sping 500 is collapsed onto the top shell 503 including eventually the filter 100 during this movement.

The attachment between the film and the bottom shell or a flexible part of the bottom shell could be also design to break when the relative pressure in the reservoir becomes smaller than −50 mbar (for example) (e.g. using stickers, grips, Velcro® like attach . . . ).

The flexible part, attached to the film, could be placed in the hard shell itself.

Before filling, the flexible part is against the hard shell (first stable position) in order to reduce the residual air volume of the reservoir.

During the priming, the flexible part will reach its second stable position against the bottom shell.

During the reservoir emptying, the flexible part will come back toward the first stable position when the reservoir under pressure is larger than 50 mbar (for example).

A bi-stable part on, either the bottom or top shell, may be actuated electromagnetically (like an electrical switch) or with a Smart Memory Alloy after detection of the under pressure in the reservoir.

The invention claimed is:

1. A device for holding a medical fluid comprising:
   a reservoir;
   a movable wall configured to change a capacity of the reservoir;
   an access port for communicating with the reservoir; and
   a biasing means configured to apply a biasing force to the movable wall,
   wherein, when emptying the medical fluid from the reservoir,
   a constant phase applies a substantially constant pressure to the reservoir when the movable wall reduces the capacity of the reservoir until a predefined volume is reached, and
   a variable phase applies a variable pressure to the reservoir by the biasing force of the biasing means after the predefined volume is reached.

2. The device according to claim 1, wherein during the constant phase, a pressure of the reservoir is equal or slightly smaller than an external pressure.

3. The device according to claim 1, wherein the predefined volume corresponds to a residual volume $V_{res}$ sufficient to ensure a safety margin to generate an alert before the reservoir is empty.

4. The device according to claim 1, wherein the biasing means increases a pressure applied to the movable wall when entering the variable phase.

5. The device according to claim 1, wherein the biasing means includes a flexible band.

6. The method for detecting a remaining volume Vres of the reservoir in the device according to claim 1, comprising the step of:
   detecting at least one of a pressure threshold and a predefined pressure gradient in the variably-sized volume.

7. The method according to claim 6, wherein the step of detecting is performed during the variable phase.

8. The method according to claim 6, wherein the step of detecting is performed during a transition from the constant phase to variable phase or during a transition from the variable phase to constant phase.

9. A pumping device for delivering a fluid, the pumping device comprising:
   a device for holding a medical fluid according to claim 1;
   a pressure sensor; and
   a pumping system in communication with the reservoir through the access port.

10. The pumping device according to claim 9, wherein during the constant phase, a pressure of the reservoir is equal or slightly smaller than an external pressure.

11. The pumping device according to claim 9, wherein the predefined volume corresponds to a residual volume $V_{res}$ sufficient to ensure a safety margin to generate an alert before the reservoir is empty.

12. The pumping device according to claim 9, wherein the biasing means increases a pressure applied to the movable wall when entering the variable phase.

13. The pumping device according to claim 9, wherein the pressure sensor is configured to detect a pressure threshold or a predefined pressure gradient to deduce a remaining volume of the reservoir during the variable phase.

14. A pumping device for delivering a fluid, the pumping device comprising:
   a reservoir including,
      a collapsible wall,
      an access port which communicates with an interior of the reservoir, and
      a biasing means configured to apply a biasing force on the collapsible wall,
      the biasing means configured to generate a behavior change of a pressure inside the reservoir when a predefined volume is reached;
   a pressure sensor; and
   a pumping system in communication with the reservoir through the access port.

15. The pumping device according to claim 14, wherein the behavior change induces a variation of a pressure gradient which is detected by the pressure sensor.

16. The pumping device according to claim 14, wherein the pressure sensor is configured to detect a remaining volume of the reservoir when the behavior change occurs.

17. The pumping device according to claim 14, wherein the behavior change includes a sudden change of the pressure inside the reservoir.

18. The pumping device according to claim 14, wherein the predefined volume corresponds to a residual volume $V_{res}$ sufficient to ensure a safety margin to generate an alert before the reservoir is empty.

19. A pumping device comprising:
   a reservoir having a main volume and a cavity, the reservoir defined by a rigid wall and a flexible wall;
   a filter; and
   an outlet;
   wherein the rigid wall includes the cavity that is in direct communication with the outlet and separated from the main volume of the reservoir by the filter, the cavity having a volume approximately equivalent to a residual volume $V_{res}$ sufficient to ensure a safety margin to generate an alert before the reservoir is empty.

20. The pumping device according to claim 19, further comprising:
   a biasing means configured to avoid a collapse of the flexible wall within the cavity until an under pressure $P_{th}$ has been reached.

21. The pumping device according to claim 20, wherein the flexible wall includes a conductive area forming a part of an electrical circuit, the electrical circuit being closed when the pressure in the reservoir is above Pth and open when the pressure in the reservoir is below Pth.

22. The pumping device according to claim 20, further comprising:
   a magnet,
   wherein the flexible wall includes an area having a ferromagnetic part configured to maintain the flexible wall in an initial position and to let the flexible wall collapse against the rigid wall when Pth has been reached.

23. The pumping device according to claim 22, further comprising:
   a second magnet,
   wherein the ferromagnetic part is configured to maintain the flexible wall close to wither the magnet or the second magnet, defining thereby two stable positions of the flexible wall.

24. The pumping device according to claim 19, wherein the cavity has a conical shape.

25. The pumping device according to claim 19, wherein the flexible wall includes a second cavity not being in direct communication with the outlet, a total volume of the cavity and the second cavity being approximately equivalent to $V_{res}$.

26. The pumping device according to claim 19, wherein the flexible wall includes a second cavity, the second cavity located opposite to the cavity of the rigid wall, the total volume of the cavity and the second cavity being approximately equivalent to Vres.

27. The pumping device according to claim 19, wherein at least one of the flexible and the rigid wall include grooves, the grooves arranged between the cavity and the outlet.

* * * * *